(12) United States Patent
Ritzberger et al.

(10) Patent No.: US 9,371,249 B2
(45) Date of Patent: Jun. 21, 2016

(54) LITHIUM DISILICATE-APATITE GLASS-CERAMIC

(71) Applicant: Ivoclar Vivadent AG, Schaan (LI)

(72) Inventors: Christian Ritzberger, Grabs (CH); Wolfram Holand, Schaan (LI); Marcel Schweiger, Chur (CH); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 14/398,599

(22) PCT Filed: Apr. 25, 2013

(86) PCT No.: PCT/EP2013/058672
§ 371 (c)(1),
(2) Date: Nov. 3, 2014

(87) PCT Pub. No.: WO2013/164256
PCT Pub. Date: Nov. 7, 2013

(65) Prior Publication Data
US 2015/0087493 A1    Mar. 26, 2015

(30) Foreign Application Priority Data
May 4, 2012   (EP) .................................... 12166760

(51) Int. Cl.
*C03C 10/04* (2006.01)
*C03C 10/00* (2006.01)
*A61K 6/00* (2006.01)
*A61K 6/06* (2006.01)
*A61K 6/02* (2006.01)
*A61K 6/027* (2006.01)

(52) U.S. Cl.
CPC ........... *C03C 10/0027* (2013.01); *A61K 6/0085* (2013.01); *A61K 6/024* (2013.01); *A61K 6/0205* (2013.01); *A61K 6/0235* (2013.01); *A61K 6/0255* (2013.01); *A61K 6/0273* (2013.01); *A61K 6/0612* (2013.01); *C03C 10/00* (2013.01)

(58) Field of Classification Search
CPC ............ C03C 10/0009; C03C 10/0018; C03C 10/0027; C03C 10/0036
USPC ............................................. 501/5, 6, 7, 8, 9
See application file for complete search history.

(56) References Cited

U.S. PATENT DOCUMENTS

| | | |
|---|---|---|
| 2,684,911 A | 7/1954 | Stookey |
| 3,006,775 A | 10/1961 | Chen |
| 3,022,180 A | 2/1962 | Morrissey et al. |
| 3,161,528 A | 12/1964 | Eppler |
| 3,252,778 A | 5/1966 | Goodman et al. |
| 3,804,608 A | 4/1974 | Gaskell et al. |
| 3,816,704 A | 6/1974 | Borom et al. |
| 3,977,857 A | 8/1976 | Mattox |
| 4,155,888 A | 5/1979 | Mooth |
| 4,189,325 A | 2/1980 | Barrett et al. |
| 4,414,282 A | 11/1983 | McCollister et al. |
| 4,473,653 A | 9/1984 | Rudoi |
| 4,480,044 A | 10/1984 | McAlinn |
| 4,515,634 A | 5/1985 | Wu et al. |
| 4,671,770 A | 6/1987 | Bell et al. |
| 4,963,707 A | 10/1990 | Zyokou et al. |
| 4,977,114 A | 12/1990 | Horinouchi et al. |
| 5,176,961 A | 1/1993 | Crooker et al. |
| 5,219,799 A | 6/1993 | Beall et al. |
| 5,507,981 A | 4/1996 | Petticrew |
| 5,628,564 A | 5/1997 | Nenyei et al. |
| 5,691,256 A | 11/1997 | Taguchi et al. |
| 5,698,482 A | 12/1997 | Frank et al. |
| 5,702,514 A | 12/1997 | Petticrew |
| 5,707,777 A | 1/1998 | Aoai et al. |
| 5,872,069 A | 2/1999 | Abe |
| 5,874,376 A | 2/1999 | Taguchi et al. |
| 5,938,959 A | 8/1999 | Wang |
| 5,968,856 A | 10/1999 | Schweiger et al. |
| 6,048,589 A | 4/2000 | Suzuki |
| 6,066,584 A | 5/2000 | Krell et al. |
| 6,095,682 A | 8/2000 | Hollander et al. |
| 6,106,747 A | 8/2000 | Wohlwend |
| 6,121,175 A * | 9/2000 | Drescher et al. ................ 501/59 |
| 6,157,004 A | 12/2000 | Bizzio |
| 6,163,020 A | 12/2000 | Bartusch et al. |
| 6,174,827 B1 | 1/2001 | Goto et al. |
| 6,252,202 B1 | 6/2001 | Zychek |
| 6,267,595 B1 | 7/2001 | Gratz |
| 6,270,876 B1 | 8/2001 | Abe et al. |

(Continued)

FOREIGN PATENT DOCUMENTS

| | | |
|---|---|---|
| CA | 2163792 A1 | 12/1994 |
| CA | 2213390 A1 | 3/1998 |

(Continued)

OTHER PUBLICATIONS

Holand et al. Studies of crystal phase formations in high-strength lithium disilicate glass-ceramics. Journal of Non-Crystalline Solids 352 (2006) 4041-4050.*
Palou et al. Mechanism and kinetics of glass-ceramics formation in the LiO2—SiO2—CaO—P2O5—CaF2 system. Cent. Eur. J. Chem. • 7(2) • 2009 • 228-233.*
Kasuga et al. Preparation of a Calcium Titanium Phosphate Glass—Ceramic with Improved Chemical Durability. J. Am. Ceram. Soc., 92 [8] 1709-1712 (2009).*
Monmaturapoj et al. Characterisation and Properties of Lithium Disilicate Glass Ceramics in the SiO2—Li2O—K2O—Al2O3 System for Dental Applications. Advances in Materials Science and Engineering vol. 2013.*
Palou, M., Mechanism and kinetics of glass-ceramics formation in the LiO2—SiO2—CaO—P2O5—CaF2 system, Central European Journal of Chemistry, 2009, vol. 7, No. 2, pp. 228-233.

(Continued)

*Primary Examiner* — Noah Wiese
(74) *Attorney, Agent, or Firm* — Ann M. Knab; Thad McMurray

(57) ABSTRACT

Lithium disilicate apatite glass-ceramics are described which are characterized by a high chemical stability and can therefore be used in particular as restoration material in dentistry.

33 Claims, No Drawings

(56) References Cited

U.S. PATENT DOCUMENTS

| | | |
|---|---|---|
| 6,287,121 B1 | 9/2001 | Guiot et al. |
| 6,342,458 B1 | 1/2002 | Schweiger et al. |
| 6,376,397 B1 | 4/2002 | Petticrew |
| 6,420,288 B2 | 7/2002 | Cramer von Clausbruch et al. |
| 6,441,346 B1 | 8/2002 | Zychek |
| 6,455,451 B1 | 9/2002 | Brodkin et al. |
| 6,485,849 B2 | 11/2002 | Petticrew |
| 6,514,893 B1 | 2/2003 | Schweiger et al. |
| 6,517,623 B1 | 2/2003 | Brodkin et al. |
| 6,593,257 B1 | 7/2003 | Nagata et al. |
| 6,802,894 B2 | 10/2004 | Brodkin et al. |
| 6,818,573 B2 | 11/2004 | Petticrew |
| 7,162,321 B2 | 1/2007 | Luthardt et al. |
| 7,316,740 B2 | 1/2008 | Rheinberger et al. |
| 7,452,836 B2 | 11/2008 | Apel et al. |
| 7,655,586 B1 | 2/2010 | Brodkin et al. |
| 7,806,694 B2 | 10/2010 | Brodkin et al. |
| 7,816,291 B2 | 10/2010 | Schweiger et al. |
| 7,867,930 B2 | 1/2011 | Apel et al. |
| 7,867,933 B2 | 1/2011 | Apel et al. |
| 7,871,948 B2 | 1/2011 | Apel et al. |
| 7,892,995 B2 | 2/2011 | Castillo |
| 7,993,137 B2 | 8/2011 | Apel et al. |
| 8,042,358 B2 | 10/2011 | Schweiger et al. |
| 8,047,021 B2 | 11/2011 | Schweiger et al. |
| 8,444,756 B2 | 5/2013 | Schweiger et al. |
| 2001/0006174 A1 | 7/2001 | Brennan |
| 2001/0031446 A1 | 10/2001 | Petticrew |
| 2002/0010063 A1 | 1/2002 | Schweiger et al. |
| 2002/0022563 A1 | 2/2002 | Schweiger et al. |
| 2002/0031670 A1 | 3/2002 | Goto et al. |
| 2002/0035025 A1 | 3/2002 | Schweiger et al. |
| 2002/0160694 A1 | 10/2002 | Wood et al. |
| 2003/0073563 A1 | 4/2003 | Brodkin et al. |
| 2004/0182538 A1 | 9/2004 | Lambrecht |
| 2005/0098064 A1 | 5/2005 | Schweiger et al. |
| 2005/0127544 A1 | 6/2005 | Brodkin et al. |
| 2006/0082033 A1 | 4/2006 | Hauptmann et al. |
| 2006/0139091 A1 | 6/2006 | Fratti |
| 2006/0257823 A1 | 11/2006 | Pfeiffer et al. |
| 2006/0257824 A1 | 11/2006 | Pfeiffer et al. |
| 2007/0023971 A1 | 2/2007 | Saha et al. |
| 2008/0120994 A1 | 5/2008 | Schweiger et al. |
| 2008/0199823 A1 | 8/2008 | Miller |
| 2009/0023574 A1 | 1/2009 | Holand et al. |
| 2009/0038344 A1 | 2/2009 | Apel et al. |
| 2009/0038508 A1 | 2/2009 | Apel et al. |
| 2009/0042166 A1 | 2/2009 | Craig et al. |
| 2009/0256274 A1 | 10/2009 | Castillo |
| 2009/0258778 A1 | 10/2009 | Castillo |
| 2010/0083706 A1 | 4/2010 | Castillo |
| 2011/0256409 A1 | 10/2011 | Ritzberger et al. |
| 2012/0094822 A1 | 4/2012 | Castillo et al. |
| 2012/0148988 A1 | 6/2012 | Castillo et al. |
| 2012/0248642 A1 | 10/2012 | Ritzberger et al. |
| 2012/0309607 A1 | 12/2012 | Duschang |
| 2014/0141960 A1 | 5/2014 | Borczuch-Laczka et al. |

FOREIGN PATENT DOCUMENTS

| | | |
|---|---|---|
| CA | 2252660 A1 | 5/1999 |
| DE | 2451121 A1 | 5/1975 |
| DE | 4303458 C1 | 1/1994 |
| EP | 0885855 A2 | 12/1998 |
| EP | 0885856 A2 | 12/1998 |
| EP | 1152641 A2 | 11/2001 |
| GB | 752243 A | 7/1956 |
| GB | 2284655 A | 6/1995 |
| JP | H10323354 A | 12/1998 |
| JP | 1174418 | 3/1999 |
| JP | 2005-062832 A | 3/2005 |
| WO | 2007/028787 A1 | 3/2007 |

OTHER PUBLICATIONS

Höland, W., et al., Studies of crystal phase formations in high-strength lithium disilicate glass-ceramics, Journal of Non-Crystalline Solids, Sep. 14, 2006, vol. 352, pp. 4041-4050.

Höland, W., et al., Mechanisms of nucleation and controlled crystallisation of needle-like apatite in glass-ceramics of the type $SiO_2$—$Al_2O_3$—$K_2O$—$CaO$—$P_2O_5$ systems, Journal of Non-Crystalline Solids, Jan. 1, 1999, vol. 253, pp. 170-177.

Mojumdar, S.C., et al., Fluoroapatite—material for medicine growth, morphology and thermoanalytical properties, Journal of Thermal Analysis and Colorimetry, 2004, vol. 78, No. 1, pp. 73-82.

Apel, E., et al., "Influence of $ZrO_2$ on the crystallization and properties of lithium disilicate glass-ceramics derived from multi-component system", Journal of European Ceramic Society, 2007, 27, 1571-1577.

Durschang, Dr. Bernhard, "Report of Results", Fraunhofer Institute for Silicate Research ISC Glass and Mineral Materials, 2015.

McMillan, P.W., et al., "The Structure and Properties of a Lithium Zinc Silicate Glass-Ceramic", Journal of Material Science 1966, I. 269-279.

Deubener, J., et al., "Induction time analysis of nucleation and crystal grown in di- and metasilicate glasses", Journal of Non-Crystalline Solids 1993, 163, 1-12.

Holand, W., et al., "Glass-ceramic technology", American Chemical Society 2002, Westerville OH, USA.

Holand, W., et al., "Control of nucleation in glass ceramics", Phil. Trans. Soc. Lond. A 2003, 361, 575-589.

Holand, W., et al., "Principles and phenomena of bioengineering with glass-ceramics of dental restoration", Journal of the European Ceramics Society 2007, 27, 1571-1577.

Ivoclar Vivadent, Inc., IPS e.max lithium disilicate, 627329, Rev. Feb. 2009.

Borom, M.P., et al., "Strength and Microstructure in Lithium Disilicate Glass Ceramics", J. Am. Ceram. Soc., 1975,58, 385-391.

Stookey, S.D., "Chemical Machining of Photosensitive Glass," Ind. Eng. Chem. 45:115-118 (1993).

Von Clausbruch, et al., "Effect of ZnO on the Crystallization, Microstructure, and Properties of Glass-Ceramics in the $SiO_2$—$Li_2O$—$K_2O$—$P_2O_5$ System," Glastech. Ber. Glass Sci. Technol. 74(8):223-229(2001).

Von Clausbruch, et al., "Effect of $P_2O_5$ on the Crystallization and Microstructure of Glass-Ceramics in the $SiO_2$—$Li_2O$—$Zn)$-$P_2O_5$ System," Glastech. Ber. Glass Sci. Technol. 74(8):223-229(2001).

Oliveria et al., "Sintering and Crystallization of a GlassPowder in the $Li_2O$—$ZrO_2$—$SiO_2$ System," J. Amer. Ceramic Soc. 81(3):777-780 (1998).

Montedo, et al., "Low Thermal Expansion Sintered LZSA Glass-Ceramics," American Ceramic Society Bulletin, vol. 87, No. 7, pp. 34-40, 1966.

Giassi, et al., "Injection Moulding of $LiO_2$—$ZrO_2$—$SiO_2$—$Al_2O_3$ (LZSA) Glass Ceramics," Glass Technol., 46(3), 277-280 (2005).

http://en.wikipedia.org/wiki/Nucleation ; Sep. 20, 2012.

* cited by examiner

LITHIUM DISILICATE-APATITE GLASS-CERAMIC

CROSS-REFERENCE TO RELATED APPLICATIONS

This application is a National Stage application of International patent application PCT/EP2013/058672 filed on Apr. 25, 2013, which claims priority to European patent application No. 12166760.4 filed on May 4, 2012, the disclosures of which are incorporated herein by reference in their entirety.

The invention relates to lithium disilicate apatite glass-ceramic which is suitable in particular for use in dentistry, preferably for the preparation of dental restorations, as well as precursors for their preparation.

Glass-ceramics with a lithium disilicate and an apatite crystal phase are known from the state of the art.

In Cent. Eur. J. Chem, 7(2), 228-233 (2009), M. Palou et al. report on the crystallization of a mixture of pure lithium disilicate glass and fluoroapatite glass. The glass ceramic produced has a high level, 14 wt.-%, of $P_2O_5$ and displays bioactivity during in-vitro tests in simulated body fluid.

In Journal of Thermal Analysis and calorimetry 78(1), 73-82 (2004), S. C. Mojumdar et al. describe studies on the crystallization of glasses from the $Li_2O$—$CaO$—$CaF_2$—$P_2O_5$—$SiO_2$ system with various levels of $P_2O_5$. After crystallization of a glass with a 15 wt.-% content of $P_2O_5$, fluoroapatite was detected in addition to a lithium disilicate crystal phase by means of X-ray diffraction.

However, the lithium silicate glass-ceramics with apatite crystal phase known from the state of the art are bioactive products and not chemically resistant materials which are suitable for restorative dentistry. In body fluids or simulated body fluids, bioactive products form apatite crystals on the surface in order, e.g. in the case of an endoprosthetic implant, to produce a solid bond with the bone.

Therefore, the known glass-ceramics have the serious disadvantage that they do not possess the chemical resistance required for a dental material which comes into contact with a wide variety of fluids in the oral cavity.

Therefore, the object of the invention is to provide a lithium disilicate apatite glass-ceramic which has a very good chemical resistance and can thus be used as restorative dental material. The glass-ceramic should also be capable of being readily processed into dental restorations, and the restorations produced from it should have very good mechanical and optical properties in addition to a very good chemical stability.

This object is achieved by the lithium disilicate apatite glass-ceramic according to claims 1 to 12 and 16. A subject of the invention is also the starting glass according to claim 13, 14 or 16, the lithium metasilicate glass-ceramic according to claim 15 or 16, the process according to claims 17 and 18 as well as the use according to claims 19 and 20.

The lithium disilicate apatite glass-ceramic according to the invention is characterized in that it comprises lithium disilicate as main crystal phase and apatite as further crystal phase and comprises 3.0 to 7.0, in particular 3.5 to 6.0 wt.-% $K_2O$.

The term "main crystal phase" refers to the crystal phase which has the highest proportion by volume compared with other crystal phases.

Surprisingly, the lithium disilicate apatite glass-ceramic according to the invention is characterized by a very high chemical stability. To determine the chemical stability, the glass ceramic was tested according to ISO standard 6872 (2008) by establishing the mass loss during storage in aqueous acetic acid. The lithium disilicate apatite glass-ceramic according to the invention displayed in particular a mass loss of less than 100 µg/cm², preferably less than 90 and particularly preferably less than 80 µg/cm² and quite particularly preferably less than 50 µg/cm².

The lithium disilicate apatite glass-ceramic preferably comprises 60.0 to 74.0, in particular 63.0 to 71.0 wt.-% $SiO_2$.

It is also preferred that the lithium disilicate apatite glass ceramic comprises 10.0 to 20.0, in particular 11.0 to 19.0 wt.-% $Li_2O$.

The molar ratio of $SiO_2$ to $Li_2O$ is in particular in the range of 1.75 to 3.0.

Furthermore, a lithium disilicate apatite glass-ceramic is preferred which comprises 3.0 to 7.0, in particular 4.0 to 6.0 wt.-% $P_2O_5$.

In a further preferred embodiment the lithium disilicate apatite glass-ceramic according to the invention comprises 0 to 5.0, in particular 0 to 4.5 wt.-% CaO and 0 to 4.0, in particular 0 to 3.5 wt.-% SrO, wherein the combined amount of CaO and SrO is 1.0 to 6.0, in particular 1.5 to 5.5 wt.-%.

A lithium disilicate apatite glass-ceramic which comprises 0.1 to 1.0, in particular 0.2 to 0.5 wt.-% F is also preferred.

The formation of fluoroapatite is possible by using fluorine. It is particularly preferred that the glass-ceramic according to the invention comprises fluoroapatite as apatite.

In a preferred embodiment the lithium disilicate apatite glass-ceramic also comprises 2.0 to 7.0, in particular 3.0 to 6.0 wt.-% oxide of trivalent elements and/or further oxide of tetravalent elements.

The oxide of trivalent elements is preferably selected from the group of $Al_2O_3$, $Y_2O_3$, $La_2O_3$ and mixtures thereof. Particularly preferably the oxide of trivalent elements is $Al_2O_3$. Even more preferably the lithium silicate apatite glass-ceramic according to the invention comprises 3.0 to 6.0 wt.-% $Al_2O_3$.

The term "further oxide of tetravalent elements" refers to oxides of tetravalent elements with the exception of $SiO_2$. Examples of suitable further oxides of tetravalent elements are $ZrO_2$, $TiO_2$ and $GeO_2$ and mixtures thereof.

Furthermore, a lithium disilicate apatite glass ceramic is preferred which comprises at least one and in particular all of the following components:

| Component | wt.-% |
| --- | --- |
| $SiO_2$ | 60.0 to 74.0 |
| $Li_2O$ | 10.0 to 20.0 |
| $P_2O_5$ | 3.0 to 7.0 |
| $K_2O$ | 3.0 to 7.0 |
| CaO | 0 to 5.0 |
| SrO | 0 to 4.0 |
| F | 0.1 to 1.0 |
| Oxide of trivalent elements and/or further oxide of tetravalent elements wherein | 2.0 to 7.0 |
| CaO + SrO is | 1.0 to 6.0. |

The lithium disilicate apatite glass-ceramic according to the invention can also comprise further additional components which in particular are selected from colorants and fluorescent agents.

Examples of colorants and fluorescent agents are oxides of d- and f-elements, such as the oxides of Ti, V, Sc, Mn, Fe, Co, Ta, W, Ce, Pr, Nd, Tb, Er, Dy, Gd, Eu and Yb. Metal colloids, e.g. of Ag, Au and Pd, can also be used as colorants and in addition can also act as nucleating agents. These metal colloids can be formed e.g. by reduction of corresponding oxides, chlorides or nitrates during the melting and crystallization processes. The metal colloids are preferably present in the glass-ceramic in an amount of from 0.005 to 0.5 wt.-%.

In a preferred embodiment the lithium disilicate apatite glass-ceramic comprises more than 20 vol.-%, preferably more than 25 vol.-% and particularly preferably more than 30 vol.-% lithium disilicate crystals, relative to the total glass-ceramic.

The glass-ceramic according to the invention with lithium disilicate as main crystal phase is characterized by particularly good mechanical properties and it can be formed e.g. by heat treatment of a corresponding starting glass or a corresponding starting glass with nuclei or a corresponding lithium metasilicate glass-ceramic.

It has surprisingly been found out that the lithium disilicate apatite glass-ceramic according to the invention has an excellent chemical stability and also has very good mechanical and optical properties. It is thus superior to the known bioactive lithium silicate apatite glass-ceramics. The combination of its properties even allows it to be used as dental material and in particular material for the preparation of dental restorations.

The lithium disilicate apatite glass ceramic according to the invention has in particular a fracture toughness, measured as $K_{IC}$ value, of at least about 1.6 MPa·m$^{0.5}$ and in particular at least about 1.8 MPa·m$^{0.5}$. This value was determined using the Vickers method and calculated using Niihara's equation. Furthermore, it has a high biaxial breaking strength of preferably from 250 to 550 MPa. The biaxial breaking strength was determined according to ISO 6872 (2008).

The invention also relates to various precursors with the corresponding composition from which the lithium disilicate apatite glass-ceramic according to the invention can be prepared by heat treatment. These precursors are a corresponding starting glass, a corresponding starting glass with nuclei and a corresponding lithium metasilicate glass-ceramic.

The invention therefore also relates to a starting glass which comprises the components of the lithium disilicate apatite glass-ceramic according to the invention.

The starting glass according to the invention therefore also comprises, in addition to 3.0 to 7.0 wt.-% $K_2O$, in particular suitable amounts of further components required to form the glass-ceramic according to the invention with lithium disilicate as main crystal phase and apatite as further crystal phase. Preferably, it comprises $SiO_2$ and $Li_2O$ in amounts which make the formation of lithium disilicate possible. Furthermore, the starting glass can also comprises still further components such as are given above for the lithium disilicate apatite glass-ceramic according to the invention. All those embodiments which are also mentioned as preferred for the components of the lithium disilicate apatite glass-ceramic according to the invention are preferred for the components of the starting glass.

The invention also relates to a starting glass which comprises nuclei for the crystallization of lithium metasilicate, lithium disilicate and/or apatite.

Furthermore, the invention relates to a lithium metasilicate glass-ceramic which comprises the components of the lithium disilicate apatite glass-ceramic according to the invention. This lithium metasilicate glass-ceramic therefore also comprises, in addition to 3.0 to 7.0 wt.-% $K_2O$, in particular suitable amounts of further components required to form the glass-ceramic according to the invention with lithium disilicate as main crystal phase and apatite as further crystal phase. Furthermore, the lithium metasilicate glass-ceramic can also comprise still further components, such as are mentioned above for the lithium disilicate apatite glass-ceramic according to the invention. All those embodiments which are also given as preferred for the components of the lithium disilicate apatite glass-ceramic according to the invention are preferred for the components of the lithium metasilicate glass-ceramic.

By heat treating the starting glass, the further precursors starting glass with nuclei and lithium metasilicate glass-ceramic can firstly be produced. The lithium disilicate apatite glass-ceramic according to the invention can then be produced by heat treating one of these two further precursors. It is preferred to form the lithium disilicate apatite glass-ceramic according to the invention directly by heat treating the starting glass with nuclei.

It is preferred to subject the starting glass to a heat treatment at a temperature of from 430 to 750° C., in particular 430 to 550° C., for a period of 5 to 120 min, in particular 10 to 60 min, in order to produce the starting glass with nuclei for the crystallization of lithium metasilicate, lithium disilicate and/or apatite.

It is further preferred to subject the starting glass with nuclei to a heat treatment at a temperature of more than 600° C. for a period of 5 to 120 min, in particular 10 to 60 min, in order to prepare the lithium metasilicate glass-ceramic or the lithium disilicate apatite glass-ceramic. To prepare the lithium disilicate apatite glass ceramic, the heat treatment of the starting glass with nuclei takes place particularly preferably at 700 to 1000° C., in particular 750 to 900° C., for a period of 5 to 120 min, in particular 10 to 60 min.

The invention also relates to a process for the preparation of the lithium disilicate apatite glass-ceramic according to the invention, wherein the starting glass, the starting glass with nuclei or the lithium metasilicate glass-ceramic is subjected to at least one heat treatment in the range of from 430 to 1000° C.

The at least one heat treatment carried out in the process according to the invention can also take place during a hot pressing or sintering-on of the starting glass according to the invention, of the starting glass according to the invention with nuclei or of the lithium metasilicate glass-ceramic according to the invention.

In a preferred embodiment the process according to the invention comprises
(a) the heat treatment of the starting glass at a temperature of from 430 to 550° C. in order to form the starting glass with nuclei, and
(b) the heat treatment of the starting glass with nuclei at a temperature of from 750 to 950° C. in order to form the lithium disilicate apatite glass-ceramic.

The duration of the heat treatments carried out in (a) and (b) is in particular 5 to 120 min and preferably 10 to 60 min.

To prepare the starting glass, the procedure is in particular that a mixture of suitable starting materials, such as carbonates, oxides, phosphates and fluorides, is melted at temperatures of in particular from 1300 to 1600° C. for 2 to 10 h. To achieve a particularly high homogeneity, the obtained glass melt is poured into water in order to form a glass granulate, and the obtained granulate is then melted again.

The melt can then be poured into moulds to produce blanks of the starting glass, so-called solid glass blanks or monolithic blanks.

It is also possible to put the melt into water again in order to prepare a granulate. This granulate can be pressed, after grinding and optionally addition of further components, such as colorants and fluorescent agents, to form a blank, a so-called powder green compact.

Finally, the starting glass can also be processed to form a powder after granulation.

The starting glass, e.g. in the form of a solid glass blank, a powder green compact or in the form of a powder, is then subjected to at least one heat treatment. It is preferred that a first heat treatment is initially carried out to prepare a starting glass according to the invention with nuclei which are suitable for forming lithium metasilicate, lithium disilicate and/or apatite crystals. This glass with nuclei is then usually subjected to at least one further temperature treatment at a higher temperature in order to effect crystallization of lithium metasilicate, lithium disilicate and/or apatite.

The further heat treatment for crystallizing lithium metasilicate takes place in particular at a temperature of at least 600° C. For crystallizing lithium disilicate, the further heat treatment takes place in particular at a temperature of at least 700° C. For crystallizing apatite, the further heat treatment takes place in particular at a temperature of at least 800° C.

The glass-ceramics according to the invention and the glasses according to the invention are present in particular in the form of powders, granulates or blanks of any form and size, e.g. monolithic blanks, such as platelets, cuboids or cylinders, or powder green compacts, in unsintered, partly sintered or densely sintered form. They can easily be further processed in these shapes. They can, however, also be present in the form of dental restorations, such as inlays, onlays, crowns, veneers, shells or abutments.

Dental restorations, such as bridges, inlays, onlays, crowns, veneers, shells or abutments, can be prepared from the glass-ceramics according to the invention and the glasses according to the invention. The invention therefore also relates to their use for the preparation of dental restorations. It is preferred that the glass ceramic or the glass is given, by pressing or machining, the shape of the desired dental restoration.

The pressing usually takes place under increased pressure and increased temperature. It is preferred that the pressing is carried out at a temperature of from 700 to 1200° C. It is further preferred to carry out the pressing at a pressure of from 2 to 10 bar. During pressing, the desired shape change is achieved by viscous flow of the material used. The starting glass according to the invention and in particular the starting glass according to the invention with nuclei, the lithium metasilicate glass-ceramic according to the invention and the lithium disilicate apatite glass-ceramic according to the invention can be used for the pressing. The glasses and glass-ceramics according to the invention can be used in particular in the form of blanks of any form and size, e.g. solid blanks or powder green compacts, e.g. in unsintered, partly sintered or densely sintered form.

The machining usually takes place by material removal processes and in particular by milling and/or grinding. It is particularly preferred that the machining is carried out in the course of a CAD/CAM process. The starting glass according to the invention, the starting glass according to the invention with nuclei, the lithium metasilicate glass-ceramic according to the invention and the lithium disilicate apatite glass-ceramic according to the invention can be used for the machining. The glasses and glass-ceramics according to the invention can be used in particular in the form of blanks, e.g. solid blanks or powder green compacts, e.g. in unsintered, partly sintered or densely sintered form. Preferably the lithium metasilicate glass-ceramic according to the invention or the lithium disilicate apatite glass-ceramic according to the invention is used for the machining. The lithium disilicate apatite glass-ceramic can also be used in a not yet fully crystallized form which was produced by heat treatment at a lower temperature. This has the advantage that an easier machining and thus the use of simpler equipment for the machining is possible. After the machining of such a partly crystallized material, the latter is usually subjected to a heat treatment at a higher temperature and in particular 700 to 1000° C. and preferably 750° C. to 900° C. in order to effect further crystallization of lithium disilicate and apatite.

In general, after the preparation of the dental restoration shaped as desired, e.g. by pressing or machining, it is in particular heat-treated again in order to convert the precursors used, such as starting glass, starting glass with nuclei or lithium metasilicate glass-ceramic, into lithium disilicate apatite glass-ceramic or to increase the crystallization of lithium disilicate and/or apatite or to reduce the porosity, e.g. of a porous powder green compact used.

However, the glass-ceramics according to the invention and the glasses according to the invention are also suitable as coating material of e.g. ceramics and glass-ceramics. The invention is therefore also directed towards the use of the glasses according to the invention or the glass-ceramics according to the invention for coating in particular ceramics and glass-ceramics.

The invention also relates to a process for coating ceramics and glass-ceramics, wherein glass-ceramics according to the invention or glasses according to the invention are applied to the ceramic or glass-ceramic and are subjected to an increased temperature.

This can take place in particular by sintering-on and preferably by pressing-on. With sintering-on, the glass-ceramic or the glass is applied to the material to be coated, such as ceramic or glass-ceramic, in the usual way, e.g. as powder, and then sintered at increased temperature. With the preferred pressing-on, glass-ceramic according to the invention or glass according to the invention is pressed on, e.g. in the form of powder green compacts or monolithic blanks, at an increased temperature of e.g. from 700 to 1200° C., and by applying pressure, e.g. 2 to 10 bar. The methods described in EP 231 773 and the press furnace disclosed therein can be used in particular for this. A suitable furnace is e.g. the Programat EP 5000 from Ivoclar Vivadent AG, Liechtenstein.

It is preferred that, after conclusion of the coating process, the glass-ceramic according to the invention is present with lithium disilicate as main crystal phase and apatite as further crystal phase, as such a glass-ceramic has particularly good properties.

Because of the above-described properties of the glass-ceramics according to the invention and the glasses according to the invention, these are suitable in particular for use in dentistry. A subject of the invention is therefore also the use of the glass-ceramics according to the invention or the glasses according to the invention as dental material and in particular for the preparation of dental restorations or as a coating material for dental restorations, such as crowns, bridges and abutments.

The invention is explained in more detail below by means of non-limiting examples.

EXAMPLES

Examples 1 to 14 and Comparison

Composition and Crystal Phases

A total of 14 glasses and glass-ceramics according to the invention with the composition given in Table I were prepared by melting corresponding starting glasses followed by heat treatment for controlled nucleation and crystallization.

A glass-ceramic not in accordance with the invention which in particular did not contain any $K_2O$ was also produced for comparison.

The heat treatments used for controlled nucleation and controlled crystallization are also given in Table I. The following meanings apply $T_N$ and $t_N$ temperature and time used for nucleation $T_{k1}$ and $t_{k1}$ temperature and time used for crystallization of lithium metasilicate $T_{k2}$ and $t_{k2}$ temperature and time used for crystallization of lithium disilicate and apatite For this, the starting glasses in a range of 100 to 200 g were first melted from customary raw materials at 1400 to 1500° C. The melting was very easily possible without formation of bubbles or streaks. By pouring the starting glasses into water, glass frits were prepared which were then melted a second time at 1450 to 1550° C. for 1 to 3 h for homogenization.

A first heat treatment of the starting glasses at a temperature of from 450 to 470° C. led to the formation of lithium silicate glasses with nuclei. As a result of a further heat treatment at 850° C., these nuclei-containing glasses crystallized to form glass-ceramics with lithium disilicate as main crystal phase and apatite as further crystal phase, as was established by X-ray diffraction tests. Lithium disilicate apatite glass-ceramics were, therefore, obtained.

In the case of Example 4 the heat treatment of the nuclei-containing starting glass at a temperature of merely 700° C. resulted in the crystallization of lithium metasilicate and thus formation of a lithium metasilicate glass-ceramic. This precursor was converted into the corresponding lithium disilicate apatite glass-ceramic by a further heat treatment at 850° C.

The produced lithium disilicate apatite glass-ceramics according to the invention showed an excellent chemical stability according to ISO test 6872 (2008). The mass loss during storage in aqueous acetic acid was less than 100 μg/cm², in particular less than 50 μg/cm².

In contrast to this, the conventional glass-ceramic, prepared for comparison, displayed a very high mass loss of 754 μg/cm² and thus a very low chemical stability. It is not suitable for use as restorative dental material which repeatedly comes into contact with fluids of the most varied composition in the oral cavity.

The lithium disilicate apatite glass-ceramics produced also had high fracture toughness values, measured as critical stress intensity factor $K_{IC}$, of more than 1.8 MPa·m$^{0.5}$.

The biaxial strength $\sigma_B$ was also high, at at least 250 MPa. It was determined according to dental standard ISO 6872 (2008) on test pieces that were prepared by machining of the respective lithium disilicate apatite glass-ceramic. A CEREC®-InLab machine (Sirona, Bensheim) was used for the machining.

The lithium disilicate apatite glass-ceramics produced and the lithium metasilicate glass-ceramic produced as precursor were able to be very satisfactorily machined into the form of various dental restorations in a CAD/CAM process or by hot pressing. These restorations were also provided with a veneer if required.

They were also able to be applied by hot pressing as coatings onto in particular dental restorations, e.g. in order to veneer the latter as desired.

TABLE I

| | Example | | | | | | | |
|---|---|---|---|---|---|---|---|---|
| | Comparison | 1 | 2 | 3 | 4 | 5 | 6 | |
| $SiO_2$ | 70.6 | 69.2 | 68.8 | 68.4 | 68.0 | 63.9 | 70.4 | |
| $P_2O_5$ | 5.0 | 5.9 | 5.9 | 5.9 | 5.9 | 5.9 | 5.9 | |
| $Li_2O$ | 17.6 | 14.4 | 14.3 | 14.2 | 14.1 | 18.2 | 11.7 | |
| $K_2O$ | — | 3.8 | 3.8 | 3.8 | 3.8 | 3.8 | 3.8 | |
| CaO | 5.9 | 2.8 | 3.3 | 3.8 | 4.3 | 4.3 | 4.3 | |
| SrO | — | — | — | — | — | — | — | |
| $Al_2O_3$ | — | 3.4 | 3.4 | 3.4 | 3.4 | 3.4 | 3.4 | |
| F | 0.9 | 0.5 | 0.5 | 0.5 | 0.5 | 0.5 | 0.5 | |
| Mol $SiO_2$:$Li_2O$ | 2.0 | 2.4 | 2.4 | 2.4 | 2.4 | 1.75 | 3.0 | |
| $T_g$/° C. | 431 | 443 | 443 | 443 | 442 | 432 | 450 | |
| $T_N$/° C. | 450 | 460 | 460 | 460 | 460 | 450 | 470 | |
| $t_N$/min. | 10 | 10 | 10 | 10 | 10 | 10 | 10 | |
| $T_{K1}$/° C. | — | — | — | — | 700 | — | — | |
| $t_{K1}$/min. | — | — | — | — | 20 | — | — | |
| $T_{K2}$/° C. | 850 | 850 | 850 | 850 | 850 | 850 | 850 | |
| $t_{K2}$/min. | 10 | 10 | 10 | 10 | 10 | 10 | 10 | |
| Main crystal phase | $Li_2Si_2O_5$ | $Li_2Si_2O_5$ | $Li_2Si_2O_5$ | $Li_2Si_2O_5$ | $Li_2Si_2O_5$ | $Li_2Si_2O_5$ | $Li_2Si_2O_5$ | |
| Further crystal phase | $Ca_5(PO_4)_3F$ | $Ca_5(PO_4)_3F$ | $Ca_5(PO_4)_3F$ | $Ca_5(PO_4)_3F$ | $Ca_5(PO_4)_3F$ | $Ca_5(PO_4)_3F$ | $Ca_5(PO_4)_3F$ | |
| Other crystal phases | $Li_3PO_4$ | $Li_3PO_4$ | $Li_3PO_4$ | $Li_3PO_4$ | $Li_3PO_4$ | $Li_2SiO_3$; $Li_3PO_4$ | quartz, $Li_3PO_4$ | |
| Chemical stability/μg·cm$^{-2}$ | 754 | — | — | — | 6 | — | — | |
| $\sigma_B$/MPa | — | — | — | — | 500.6 | — | — | |
| $K_{IC}$/MPa·m$^{0.5}$ | — | — | — | — | 2.30 | — | — | |

| | Example | | | | | | | |
|---|---|---|---|---|---|---|---|---|
| | 7 | 8 | 9 | 10 | 11 | 12 | 13 | 14 |
| $SiO_2$ | 66.5 | 66.2 | 68.7 | 69.4 | 68.7 | 68.7 | 70.4 | 68.9 |
| $P_2O_5$ | 5.8 | 5.8 | 5.0 | 4.0 | 6.0 | 6.0 | 5.1 | 5.0 |
| $Li_2O$ | 13.8 | 13.7 | 14.3 | 14.4 | 14.3 | 14.3 | 14.6 | 14.3 |
| $K_2O$ | 5.9 | 3.7 | 3.9 | 3.9 | 3.9 | 3.9 | 4.0 | 3.9 |
| CaO | 4.2 | 4.2 | 4.3 | 4.4 | — | 1.5 | 2.0 | 4.4 |
| SrO | — | — | — | — | 3.3 | 1.9 | — | — |
| $Al_2O_3$ | 3.3 | 5.9 | 3.4 | 3.4 | 3.4 | 3.4 | 3.5 | 3.4 |
| F | 0.5 | 0.5 | 0.5 | 0.5 | 0.5 | 0.4 | 0.5 | 0.2 |
| Mol $SiO_2$:$Li_2O$ | 2.4 | 2.4 | 2.4 | 2.4 | 2.4 | 2.4 | 2.4 | 2.4 |

TABLE I-continued

| | | | | | | | | |
|---|---|---|---|---|---|---|---|---|
| $T_g/°C$ | 444 | 444 | 441 | 443 | 443 | 435 | 442 | 450 |
| $T_N/°C$ | 460 | 460 | 460 | 460 | 460 | 450 | 460 | 470 |
| $t_N$/min. | 10 | 10 | 10 | 10 | 10 | 10 | 10 | 10 |
| $T_{K1}/°C$ | — | — | — | — | — | — | — | — |
| $t_{K1}$/min. | — | — | — | — | — | — | — | — |
| $T_{K2}/°C$ | 850 | 850 | 850 | 850 | 850 | 850 | 850 | 850 |
| $t_{K2}$/min. | 10 | 10 | 10 | 10 | 10 | 10 | 10 | 10 |
| Main crystal phase | $Li_2Si_2O_5$ | $Li_2Si_2O_5$ | $Li_2Si_2O_5$ | $Li_2Si_2O_5$ | $Li_2Si_2O_5$ | $Li_2Si_2O_5$ | $Li_2Si_2O_5$ | $Li_2Si_2O_5$ |
| Further crystal phase | $Ca_5(PO_4)_3F$ | $Ca_5(PO_4)_3F$ | $Ca_5(PO_4)_3F$ | $Ca_5(PO_4)_3F$ | $Sr_5(PO_4)_3F$ | $Sr_{7.3}Ca_{2.7}(PO_4)_6F_2$ | $Ca_5(PO_4)_3F$ | $Ca_5(PO_4)_3F$ |
| Other crystal phase | $Li_3PO_4$ | $Li_3PO_4$ | $Li_3PO_4$ | $Li_2SiO_3$, $Li_3PO_4$ | $Li_3PO_4$ | $Li_3PO_4$ | $Li_3PO_4$ | $Li_3PO_4$ |
| Chemical stability/ $\mu g \cdot cm^{-2}$ | — | — | — | 13.0 | — | 13.0 | — | 11.0 |
| $\sigma_B$/MPa | — | — | — | 500 | — | 401 | — | 285 |
| $K_{IC}$/MPa·m$^{0.5}$ | — | — | — | — | — | — | — | — |

The invention claimed is:

1. Lithium disilicate apatite glass-ceramic, which comprises lithium disilicate as main crystal phase and apatite as further crystal phase and which comprises 3.0 to 7.0 wt.-% $K_2O$, 0 to 5.0 wt.-% CaO and 0 to 4.0 wt.-% SrO, wherein the combined amount of CaO and SrO is 1.0 to 6.0 wt.-%.

2. Lithium disilicate apatite glass-ceramic according to claim 1, which comprises 60.0 to 74.0 wt.-% $SiO_2$.

3. Lithium disilicate apatite glass-ceramic according to claim 1, which comprises 10.0 to 20.0 wt.-% $Li_2O$.

4. Lithium disilicate apatite glass-ceramic according to claim 1, which contains 3.0 to 7.0 wt.-% $P_2O_5$.

5. Lithium disilicate apatite glass-ceramic according to claim 1, which comprises 0.1 to 1.0 wt.-% F.

6. Lithium disilicate apatite glass-ceramic according to claim 1, which comprises 2.0 to 7.0 wt.-% oxide of trivalent elements and/or further oxide of tetravalent elements.

7. Lithium disilicate apatite glass-ceramic according to claim 6, wherein the oxide of trivalent elements is selected from the group of $Al_2O_3$, $Y_2O_3$, $La_2O_3$ and mixtures thereof.

8. Lithium disilicate apatite glass-ceramic according to claim 6, wherein the further oxide of tetravalent elements is selected from the group of $ZrO_2$, $TiO_2$, $GeO_2$ and mixtures thereof.

9. Lithium disilicate apatite glass-ceramic according to claim 1, which comprises at least one and preferably all of the following components:

| Component | wt.-% |
|---|---|
| $SiO_2$ | 60.0 to 74.0 |
| $Li_2O$ | 10.0 to 20.0 |
| $P_2O_5$ | 3.0 to 7.0 |
| $K_2O$ | 3.0 to 7.0 |
| CaO | 0 to 5.0 |
| SrO | 0 to 4.0 |
| F | 0.1 to 1.0 |
| Oxide of trivalent elements and/or further oxide of tetravalent elements wherein | 2.0 to 7.0 |
| CaO + SrO is | 1.0 to 6.0. |

10. Lithium disilicate apatite glass-ceramic according to claim 1, which comprises fluoroapatite as apatite.

11. Lithium disilicate apatite glass ceramic, which comprises lithium disilicate as main crystal phase and apatite as further crystal phase and which comprises 3.0 to 7.0 wt.-% $K_2O$ and which comprises more than 20 vol.-% lithium disilicate crystals.

12. Starting glass, which comprises the components of the glass-ceramic according to claim 1.

13. Starting glass according to claim 12, which comprises nuclei for the crystallization of lithium metasilicate, lithium disilicate and/or apatite.

14. Lithium metasilicate glass-ceramic, which comprises lithium metasilicate as main crystal phase and apatite as further crystal phase and which comprises 3.0 to 7.0 wt.-% $K_2O$, 0 to 5.0 wt.-% CaO and 0 to 4.0 wt.-% SrO, wherein the combined amount of CaO and SrO is 1.0 to 6.0 wt.-%.

15. Glass-ceramic according to claim 1, wherein the glass-ceramic is present in the form of a powder, a granulate, a blank or a dental restoration.

16. Process for the preparation of the glass-ceramic according to claim 1, wherein a starting glass or a lithium metasilicate glass-ceramic is subjected to at least one heat treatment in the range of from 430° to 1000° C.

17. Process according to claim 16, wherein
(a) the starting glass is subjected to a heat treatment at a temperature of from 430 to 550° C. in order to form starting glass with nuclei, and
(b) the starting glass with nuclei is subjected to a heat treatment at a temperature of from 750 to 950° C. in order to form the lithium disilicate apatite glass-ceramic.

18. A method of using the glass-ceramic according to claim 1, as dental material comprising coating dental restorations and preparing dental restorations.

19. The method of using the glass-ceramic according to claim 18, wherein the method comprises pressing or machining, the shape of the desired dental restoration, bridge, inlay, onlay, veneer, abutment, partial crown, crown or shell.

20. Lithium disilicate apatite glass-ceramic, which comprises lithium disilicate as main crystal phase and apatite as further crystal phase and which comprises 3.5 to 6.0 wt.-% $K_2O$.

21. Lithium disilicate apatite glass-ceramic according to claim 2, which comprises 63.0 to 71.0 wt.-% $SiO_2$.

22. Lithium disilicate apatite glass-ceramic according to claim 1, which comprises 11.0 to 19.0 wt.-% $Li_2O$.

23. Lithium disilicate apatite glass-ceramic, which comprises lithium disilicate as main crystal phase and apatite as further crystal phase and which contains 4.0 to 6.0 wt.-% $P_2O_5$ and 3.0 to 7.0 wt.-% $K_2O$.

24. Lithium disilicate apatite glass-ceramic according to claim 1, which comprises 0 to 4.5 wt.-% CaO and 0 to 3.5 wt.-% SrO, wherein the combined amount of CaO and SrO is 1.5 to 5.5 wt.-%.

25. Lithium disilicate apatite glass-ceramic according to claim 1, which comprises 0.2 to 0.5 wt.-% F.

26. Lithium disilicate apatite glass-ceramic according to claim 1, which comprises 3.0 to 6.0 wt.-% oxide of trivalent elements and/or further oxide of tetravalent elements.

27. Lithium disilicate apatite glass-ceramic according to claim 26, wherein the oxide of trivalent elements is selected from the group of $Al_2O_3$, $Y_2O_3$, $La_2O_3$ and mixtures thereof.

28. Lithium disilicate apatite glass ceramic according to claim 11, which comprises more than 25 vol.-% lithium disilicate crystals.

29. Lithium disilicate apatite glass ceramic according to claim 11, which comprises more than 30 vol.-% lithium disilicate crystals.

30. Starting glass according to claim 12, wherein the starting glass is present in the form of a powder, a granulate, a blank or a dental restoration.

31. Lithium metasilicate glass-ceramic according to claim 14, wherein the lithium metasilicate glass-ceramic is present in the form of a powder, a granulate, a blank or a dental restoration.

32. A method of using the starting glass according to claim 12 as dental material comprising coating dental restorations and preparing dental restorations.

33. A method of using the lithium metasilicate glass-ceramic according to claim 14 as dental material comprising coating dental restorations and preparing of dental restorations.

* * * * *